United States Patent [19]
Pont

[11] 4,217,782
[45] Aug. 19, 1980

[54] ULTRASONIC INSPECTION DEVICE AND METHOD OF INSPECTION

[75] Inventor: Glen W. Pont, Lafayette, La.
[73] Assignee: W. C. Lamb, Lafayette, La.
[21] Appl. No.: 927,946
[22] Filed: Jul. 25, 1978
[51] Int. Cl.³ ............................................. G01N 29/04
[52] U.S. Cl. ...................................... 73/637; 73/638; 73/639
[58] Field of Search ................ 73/635, 637, 639, 640, 73/622, 638

[56] References Cited
U.S. PATENT DOCUMENTS

| 3,169,393 | 2/1965 | Stebbins | 73/622 |
| 3,228,233 | 1/1966 | Keldenich | 73/622 |
| 3,628,375 | 12/1971 | Pagano | 73/639 |
| 4,020,688 | 5/1977 | Hauldren | 73/638 |
| 4,099,418 | 7/1978 | Bennett et al. | 73/622 |

*Primary Examiner*—Anthony V. Ciarlante
*Attorney, Agent, or Firm*—Arnold, White & Durkee

[57] ABSTRACT

An ultrasonic inspection device for nondestructive inspection of cylindrical members includes a pair of resilient inspection wheels which house multiple ultrasonic transducers. The inspection wheels are mounted in a carriage so as to ride along the surface of a rotating cylindrical member being inspected. Relative longitudinal motion between the carriage and the cylindrical member allows the inspection wheels to transcribe helical paths over the surface of the member.

18 Claims, 10 Drawing Figures

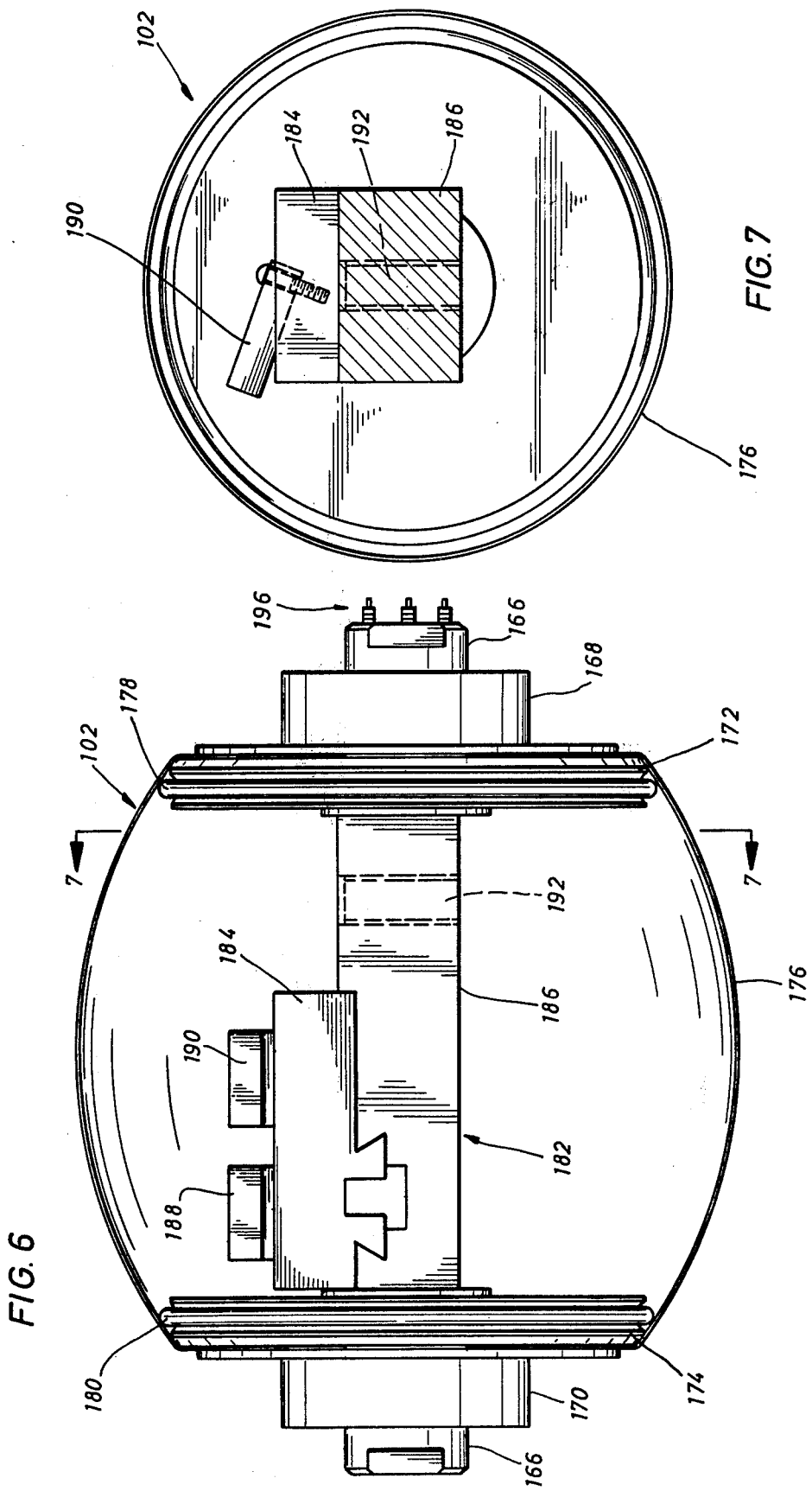

ULTRASONIC INSPECTION DEVICE AND METHOD OF INSPECTION

CROSS REFERENCE TO RELATED APPLICATIONS

The subject matter of this application is related to commonly assigned copending applications Ser. No. 927,945, entitled "APPARATUS AND METHOD FOR ULTRASONIC INSPECTION OF TUBULAR MEMBERS" and Ser. No. 927,944, entitled "PIPE INSPECTION SYSTEM AND METHOD", both filed on even date herewith.

BACKGROUND OF THE INVENTION

1. Field of the Invention

The invention relates to search units used in nondestructive ultrasonic testing. In particular, the invention relates to inspection wheel assemblies which house multiple ultrasonic transducers and are adapted to ride on the surface of a rotating cylindrical member to test for defects, for example, longitudinal and transverse defects.

2. Description of the Prior Art

The use of ultrasonic testing techniques, and specifically of ultrasonic crystals, for detecting discontinuities in metal products is a common mode of nondestructive testing. The crystals employed are typically piezoelectric crystals made of a material such as quartz. These crystals produce ultrasonic vibrations in response to a voltage of appropriate frequency impressed upon the crystal. When inspecting a tubular product for internal flaws using a reflection method, the crystal is maintained in a position relative to the surface of the product to transmit a short duration sonic wave pulse into the product at an angle such that a defect or discontinuity will cause the waves to be reflected to the crystal and produce a voltage response in the crystal. Since the crystal is de-energized immediately following the pulsed emission of a wave, reflected waves are received during de-energized periods and hence the reflected waves will produce a discernible signal which may be monitored, for example, on a cathode ray tube or a strip chart recorder. Pulse repetition rates of between 60 and 2000 pulses per second are employed for various types of inspections.

Typically, an ultrasonic inspection device will be calibrated using a standard identical to the goods being inspected. The standard may have one or more discontinuities of known magnitude so that the response of the device to known imperfections may be ascertained, and standards for accepting or rejecting the inspected goods may be established.

Ultrasonic inspection techniques are most typically employed at the site of manufacture of the articles being inspected. Thus, plate or tubular goods are typically inspected at the manufacturing plant using techniques which are well known in the art. However, the on-site inspection of new and previously used tubular goods presents different and unique problems.

In well drilling operations, drill pipe failures can be a costly and time-consuming occurrence. Washouts or drill string breakage can occur frequently if a drill pipe with sufficiently serious imperfections is employed. Most frequently such failures result from internal flaws in the tubular goods being used. Confronted with such a failure, it becomes necessary to trip the pipe out of the borehole to replace the failed joint. In the case of drill string breakage, it is also necessary to fish the parted portion of the string from the borehole before drilling can be recommenced. Hence, the value of an efficacious method of inspection, particularly for monitoring wall thickness and detecting internal flaws in drill pipe, is obvious.

An apparatus and method for ultrasonic inspection of tubular goods employed in the drilling of oil and gas wells is disclosed in U.S. Pat. No. 4,020,688, commonly assigned with this application to W. C. Lamb. According to this patented apparatus and method, drill pipe, well casing or tubing may be inspected as it is being tripped into or out of a well borehole, i.e., while the tubular member is in a substantially vertical mode. The apparatus includes a number of search units, preferably wheel search units, which house transducers and are positioned at 90° centers around the pipe being inspected. The beam spread of the search units determines whether the entire circumference of the pipe is being inspected as it passes through the apparatus.

A review of the art reveals that there is an acute need for an apparatus and method for inspection of both new and previously used oil field tubular goods while such tubular goods are being stored preparatory to downhole use.

SUMMARY OF THE INVENTION

In accordance with the instant invention, there is provided a novel ultrasonic inspection device for the nondestructive ultrasonic testing of cylindrical members having a bore, for example, oil field tubular goods. In one aspect, the invention comprises an ultrasonic inspection wheel having an axle, a fixed central yoke disposed between the ends of the axle, a plurality of ultrasonic transducers mounted on the yoke, flanges rotatably mounted proximate the ends of the yoke and a flexible bladder having two open ends with each end being mounted on a respective one of said flanges.

In another aspect, the invention comprises a first ultrasonic search device including a wall thickness transducer and a pair of circumferential scan transducers for transmitting sonic beams in opposite directions around the member being inspected, a second ultrasonic search device including a wall thickness transducer and a pair of lengthwise scan transducers for transmitting sonic beams in opposite directions lengthwise on the member to detect transverse flaws, the transducers of said first and second devices being held in a fixed spatial relationship with respect to each other, means for rotating the member being inspected and for providing relative longitudinal movement between the first and second device and the member, and means for sonically coupling said devices to the member being inspected.

Yet another aspect the invention comprises a method of nondestructive testing of oil field tubular goods wherein the member to be inspected is rotated about its axis, a pair of ultrasonic inspection devices are displaced longitudinally with respect to the member with each inspection device including at least three ultrasonic transducers, the inspection devices are sonically coupled to the member, a pair of transducers in one ultrasonic device circumferentially scans the member to detect longitudinal flaws, a pair of transducers in the second inspection device scans the member lengthwise to detect transverse flaws and a wall thickness transducer in each inspection device monitors the wall thickness.

BRIEF DESCRIPTION OF THE DRAWINGS

FIG. 6 is a side view of the circumferential scan wheel assembly with a portion of the bladder broken away to show the transducers.

FIG. 7 is a partial section view taken along line 7—7 of FIG. 6 showing the orientation of the ultrasonic transducers.

DESCRIPTION OF THE PREFERRED EMBODIMENT

Figure 1:
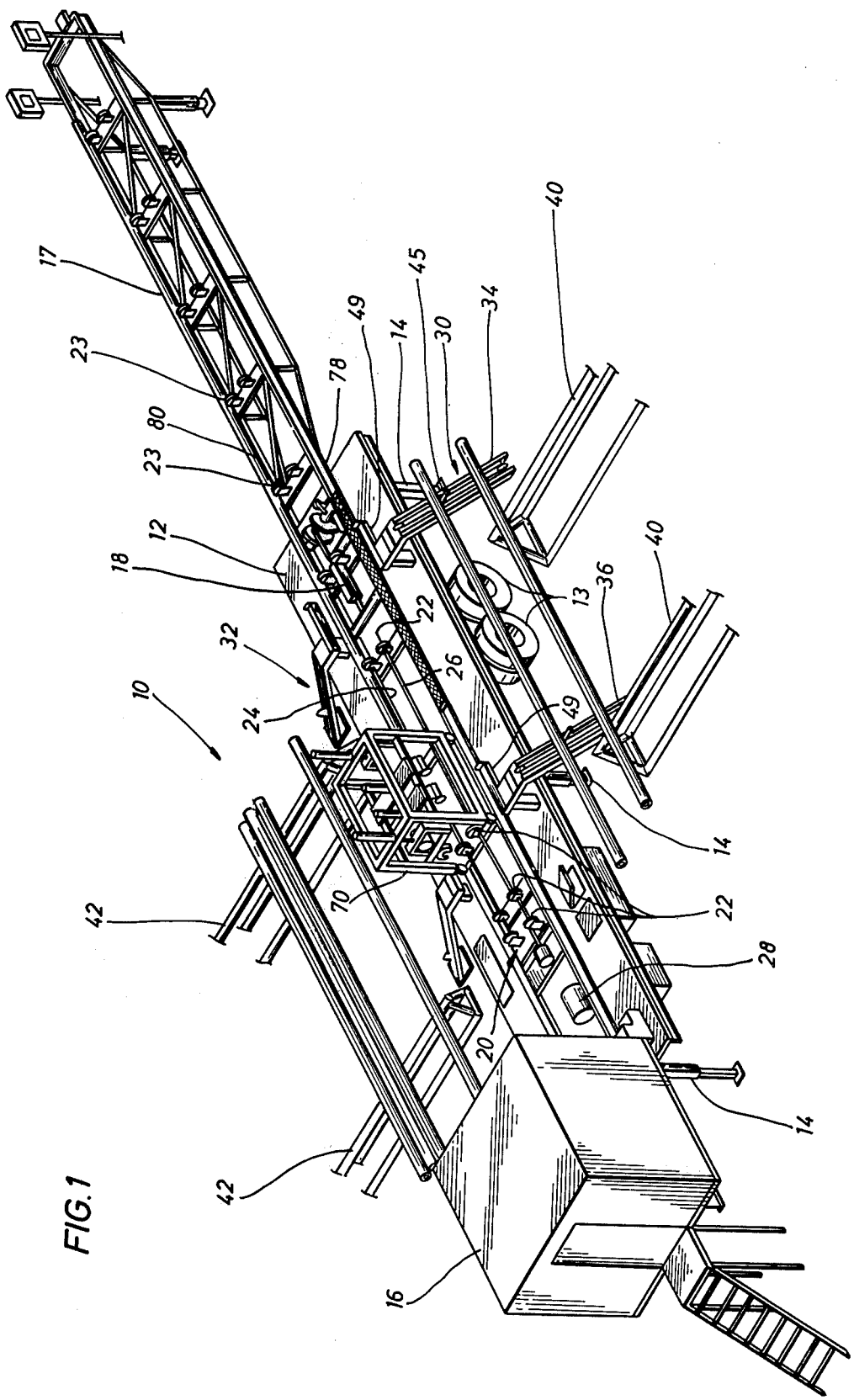
FIG. 1 is a pictorial view of the preferred embodiment of an ultrasonic inspection system constructed in accordance with the present invention.

Referring now to FIG. 1, there is shown in perspective a portable ultrasonic inspection system 10 constructed in accordance with the present invention. System 10 includes a substantially horizontal support deck or flatbed trailer 12 supported by a plurality of wheels 13 and being of the type adapted for movement to the site of an oil drilling operation by means of a tractor cab (not shown). During pipe inspection operations, deck 12 is stabilized by a plurality of vertical support members 14. A control house 16 is made integral with deck 12 and serves to house the various control apparatus and the operator. An auxiliary truss section 17 is hingedly connected to the rear of deck 12 for supporting a portion of long pipe sections, e.g., 45 to 50 feet in length. An hydraulic cylinder 18 serves to move truss section 17 from its operative extended position shown in FIG. 1 to a nonoperative position over deck 12 for transport of the system.

Deck 12 supports a pipe drive assembly 20 which includes four sets of drive rollers 22 mounted on drive shafts 24, 26. Rollers 22 are driven through appropriate transmission means by an hydraulic motor 28. The sets of rollers 22 are spaced along their respective drive shafts and are laterally spaced from each other so as to support the pipe being inspected. If desired, means may be provided so that the lateral spacing between the rollers may be adjusted according to the diameter of the pipe being inspected. As best shown in FIG. 1, rollers 22 comprise circular discs which rotate in a plane normal to the drive shafts; therefore, rotation of the rollers will cause a pipe resting thereon to rotate about its longitudinal axis at a rotational speed which may be easily controlled through operation of the hydraulic motor. A plurality of idler rollers 23 are mounted on truss section 17 to support the end portion of relatively long pipe being inspected.

The means for loading and unloading pipe onto deck 12 comprises a pipe load assembly 30 and a pipe unload assembly 32. Load assembly 30 includes a pair of load ramps 34, 36 each having aligned, cable-driven or chain-driven dogs for engaging and lifting successive pipes from a pipe loading rack generally designated by reference numeral 40. Likewise, unload system 32 includes a pair of ramps having aligned dogs for transferring pipe to a storage rack 42 where the pipe sections having defects may be separated from the acceptable pipe.

Figure 2:
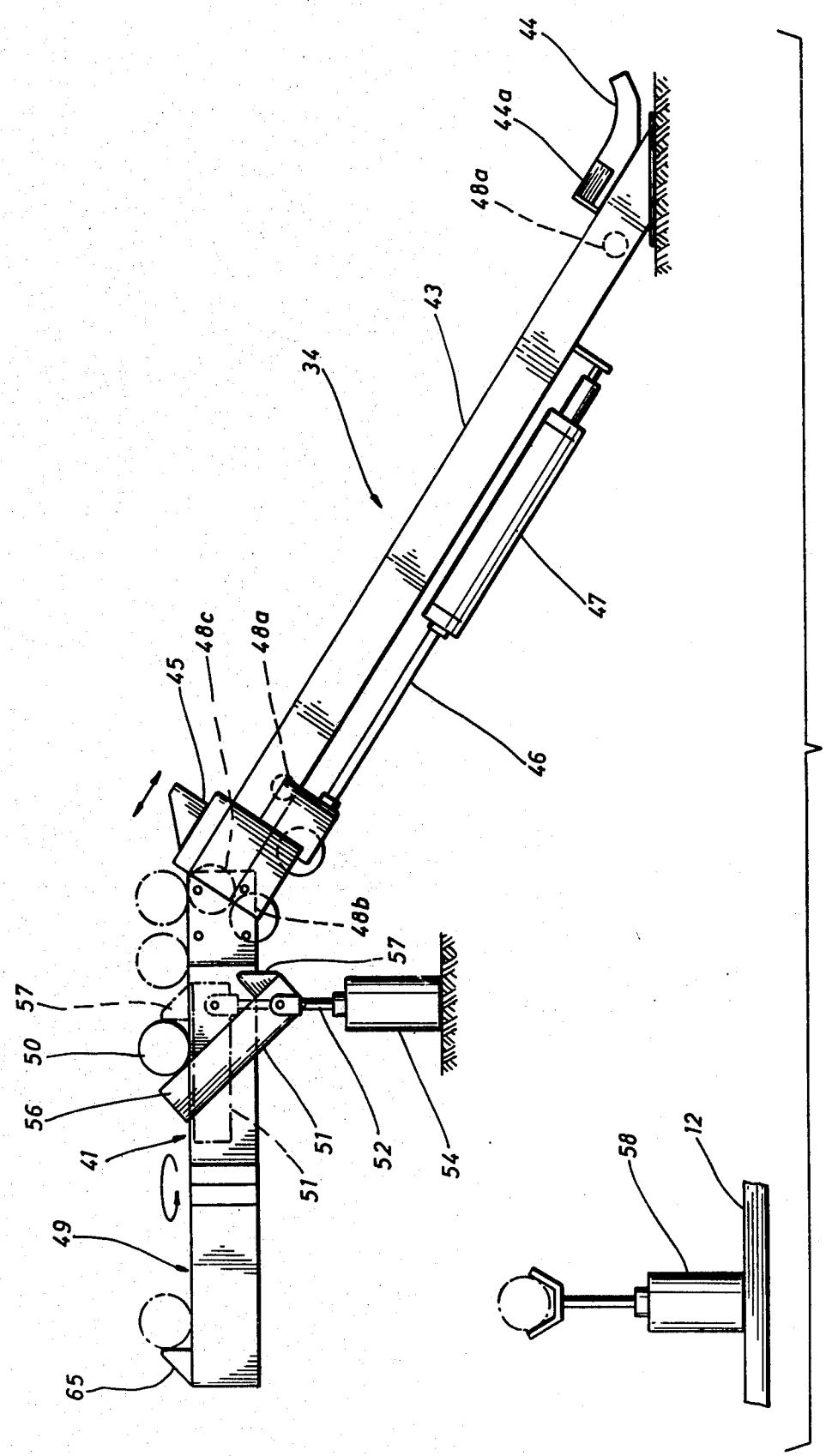
FIG. 2 is a side view of a pipe load ramp and associated swing arm.

As best shown in FIG. 2, load ramp 34 includes an inclined frame member 43 which pivotally mounts an endoe arm 44 at its lower end. Endoe 44 is adapted to receive pipe from rack 42 by a manual operation. Each endoe 44 includes a roller 44a over which the pipe may be moved to bring the pipe to the desired position before raising it.

A lift dog 45 is mounted on a pulley system for lifting pipe from endoe 44 and moving it upwardly along the entire length of ramp 34. In the preferred embodiment, dog 45 is powered by means of rod 46 of a cylinder 47 through a pulley system, for example a 4-to-1 pulley system including pulleys 48a, 48b, 48c and 48d.

As each successive pipe is lifted to the top of ramps 34, 36 by dogs 45 it is loaded onto a load deck 41 where a number of pipes may rest awaiting transfer to the rollers 22. Referring to FIG. 2, it will be seen that the centermost pipe, for example, pipe 50, resting on deck 41 will be restrained from further motion toward the center of deck 12 by a stop member 51 in its first position shown in solid lines in FIG. 2. Member 51 is secured at one end to the rod 52 of a kick cylinder 54. When rod 52 is retracted to place member 51 in the position shown in solid lines, the forward end 56 of member 51 restrains pipe 50 from further movement. In response to an automatic or manually given command signal, rod 52 moves upwardly so that member 51 moves to its second position shown in dashed lines in FIG. 2. With member 51 in this position, pipe 50 is free to roll along deck 41 onto swing arms 49. According to the illustrated embodiment, member 51 includes a triangular projection 57 that serves a dual function. When member 51 moves from the first position (solid lines) to the second position, projection 57 engages the trailing surface of pipe 50 and moves it along toward the rollers. With member 51 in the second position, projection 57 prevents the next successive pipe from following pipe 50. It will be appreciated that the position of projection 57 on member 51 may be varied according to the size of pipe being inspected.

As pipe 50 leaves deck 41 it moves onto the swing arms 49 each of which has been moved by a fluid cylinder (not shown) from its retracted position shown in FIG. 1 to its extended position shown in FIG. 2. Each swing arm 49 includes at its end a pipe stop 65. The stops hold the pipe in a position centered over the space between the laterally spaced drive rollers 22. The position of the stops may be adjusted according to the size of the pipe being inspected.

After the pipe is centered above the drive wheels on swing arms 49, a plurality of lift cylinders 58 (only one shown) extend to lift the pipe off the swing arms thus freeing the swing arms to retract. As best shown in FIG. 2, between the laterally spaced rollers 22, the end of the rod of lift cylinder 58 forms a substantially V- shaped portion for receiving the pipe. When the pipe rests in the V-shaped portions of the extended lift cylinders, the swing arms 49 retract and the lift cylinders 58 are lowered to set the pipe in the drive area between rollers 22. The unloading of pipe from the rollers after inspection is essentially the reverse of the loading operation with the lift cylinders transferring the pipe to the swing arms of the unload assembly 32. The automatic sequential operation of the pipe load/unload system will be described in detail below with reference to FIG. 9.

In the embodiment illustrated in FIG. 1, the pipe being inspected is supported and rotated by drive rollers 22 without any longitudinal motion being imparted to the pipe. The inspection wheels housing the ultrasonic transducers are driven over the length of the pipe by means of a carriage 70 which is shown in detail in FIG. 3. Carriage 70 comprises a substantially box-shaped frame 72 including a plurality of rigid peripheral support members. Carriage 70 is supported by a plurality of rollers 76 which ride on longitudinal tracks 78, 80 (FIG. 1) along the entire length of deck 12 and truss section 17. Carriage 70 may be driven along the tracks by any suitable drive means. In the preferred embodiment, a chain drive assembly powered by an hydraulic motor (not shown) is employed to drive the carriage in response to command signals from the program control in the manner set forth in detail below.

Figure 3:
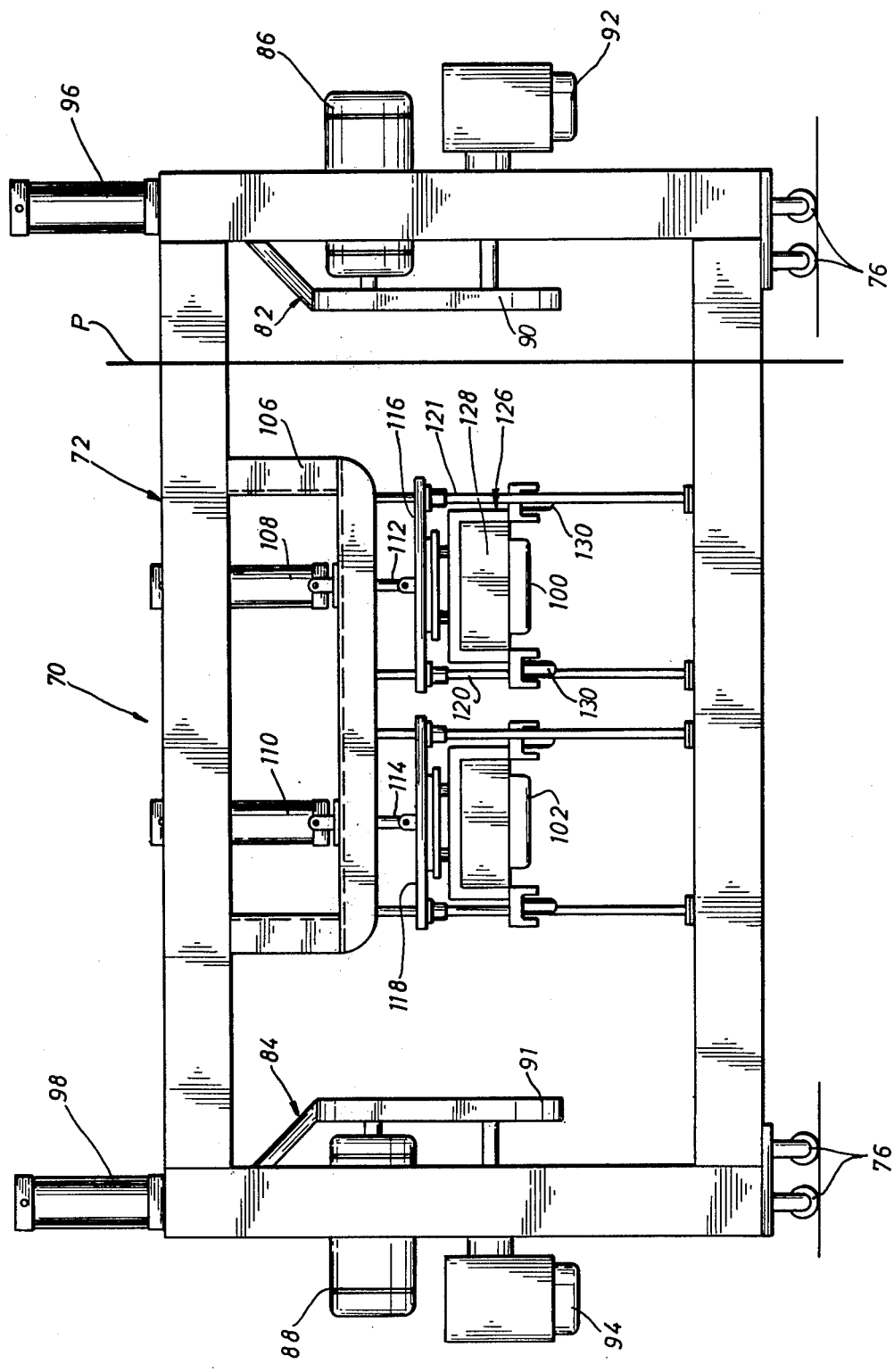
FIG. 3 is a side view of the carriage which mounts the two inspection wheels.

The ends of the carriage include vertically movable brackets 82, 84. The brackets mount a pair of electric or hydraulic motors 86, 88 which are adapted to drive pipe cleaning brushes 92, 94 respectively through bolt or chain drive systems housed in housings 90, 91. Each motor and its associated brush form an assembly which may be vertically displaced by means of one of pneumatic cylinders 96, 98. Cylinders 96, 98 are actuated in response to commands from the program control to move brushes 92, 94 into and out of contact with the pipe for cleaning the exterior portion of the pipe, especially previously used pipe, prior to inspection. For example, as carriage 70 moves to the right as shown in FIG. 3, brush 92 is driven by motor 86 and moved downwardly by cylinder 96 to be brought into contact with the portion of the pipe to be next inspected; when carriage 70 is moving to the left, brush 94 is utilized in a like manner.

The interior portion of carriage 70 includes the equipment which is designed to hold the inspection wheels 100, 102 in contact with the pipe at a substantially constant force. A cylinder mount 106 is secured to the upper cross members of carriage 70 and mounts a pair of vertically oriented pneumatic cylinders 108, 110. The rods 112, 114 of cylinders 108, 110 are secured to a pair of flat plates or guide frames 116, 118. For convenience of description, the wheel support structure associated with guide frame 116 and wheel 100 will be described in detail, with the understanding that the structure supporting wheel 102 is identical. Guide frame 116 rides on stationary vertical guide rods 120, 121 which are secured at their upper and lower ends to carrier cross members. The vertically displaceable guide frame 116 is, in turn, detachably secured to a head assembly 126. Assembly 126 includes a wheel housing 128 having journals (not shown) for supporting the axles of the inspection wheel. Assembly 126 also includes four (only two shown) support wheels 130 which ride along the surface of the pipe being inspected. Although not illustrated in detail in FIG. 3, support wheels 130 are inclined at a fixed angle relative to a plane P which is perpendicular to the pipe axis. This inclination allows the head assembly to smoothly track the helical path transcribed on the pipe being inspected. Preferably, the angle of inclination is equal to the pitch angle of the helix being transcribed on the surface of the pipe. The pitch angle varies according to the linear speed of the carriage and the rotational speed of the pipe. It has been found that under optimal operating conditions the pitch angle for a two and three eighths inch (2⅜") pipe is approximately eleven degrees whereas the pitch angle for a sixteen inch (16") pipe is approximately one degree. It has also been found that support rollers 130 do not have to be oriented exactly at the pitch angle of the helix being transcribed in order to give satisfactory tracking. Therefore, a few different pitch angle settings are all that is necessary for inspection of typical oil field tubular goods ranging in outside diameter from approximately two and three eighths inches (2⅜") to sixteen (16") inches. Although the angle of inclination of the support wheels 130 may be made to be manually adjustable for each pipe size, in the preferred embodiment the head assemblies 126 are made interchangeable with each different assembly having the wheels mounted at a different, fixed angle.

Figure 4:
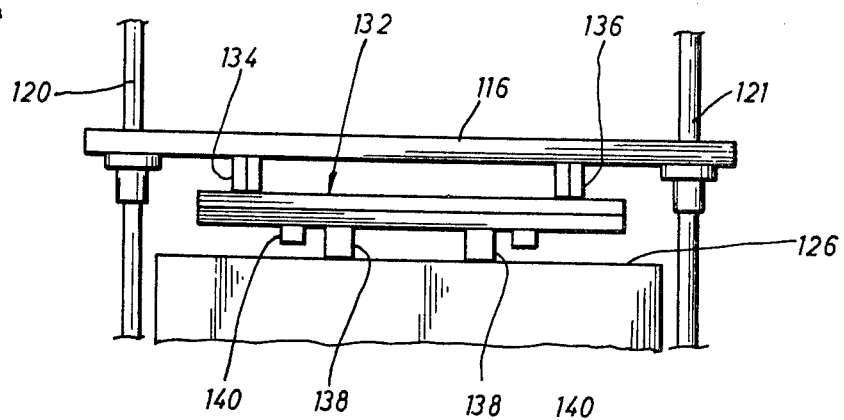
FIG. 4 is an enlarged view of the shock absorbing structure at the interface between a carriage guide frame and its associated head assembly.

The detachable securement between guide frame 116 and its associated head assembly 126 is best shown in FIG. 4. Because of irregularities in the diameter of the pipe being inspected, bows in the pipe, and other irregularities in the pipe, the support wheels 130 and inspection wheel 100 must constantly move to remain in contact with the rotating pipe. For reasons explained below in connection with the description of the inspection wheels, the contact should continue at a substantially constant pressure. Therefore, a shock absorbing connection is made between the guide frames and their associated head assemblies. Referring to FIG. 4, guide frame 116 attaches to a two-piece adaptor plate 132 by means of linear bearings 134, 136. The bearings allow relative horizontal movement between the guide frame and the adaptor plate in a plane perpendicular to the axis of the pipe being inspected. The adaptor plate is, in turn, secured to the upper surface of head assembly 126 by means of four rubber grommets 138 (only two shown). The grommets are relatively compressible so as to absorb shock and provide some degree of play in a horizontal plane. The two pieces of the adaptor plate are held together by a plurality of bolts 140 or other suitable detachable securement means. Removal of bolts 140 allows the head assembly, including the lower piece of the adaptor plate, to be removed for replacement by another assembly having the support wheels 130 secured at a different pitch angle.

Although not illustrated, carriage 70 includes at least one spray nozzle for applying a film of water between the search wheels and the pipe being inspected. As is well known to those skilled in the art, the water film serves as a coupling fluid which allows the sound beams to pass from the wheel into the pipe. Significant advantages are achieved by coupling with a spray instead of the very unwieldy immersion technique widely used in the art. It should be pointed out that the portion of the inspection wheel in contact with and coupled to the pipe, i.e., the "footprint", must be large enough to extend to all areas where sound beams are leaving the inspection wheel and entering the pipe. Therefore, a substantially constant pressure must be maintained between the inspection wheels and the pipe.

Figure 5:
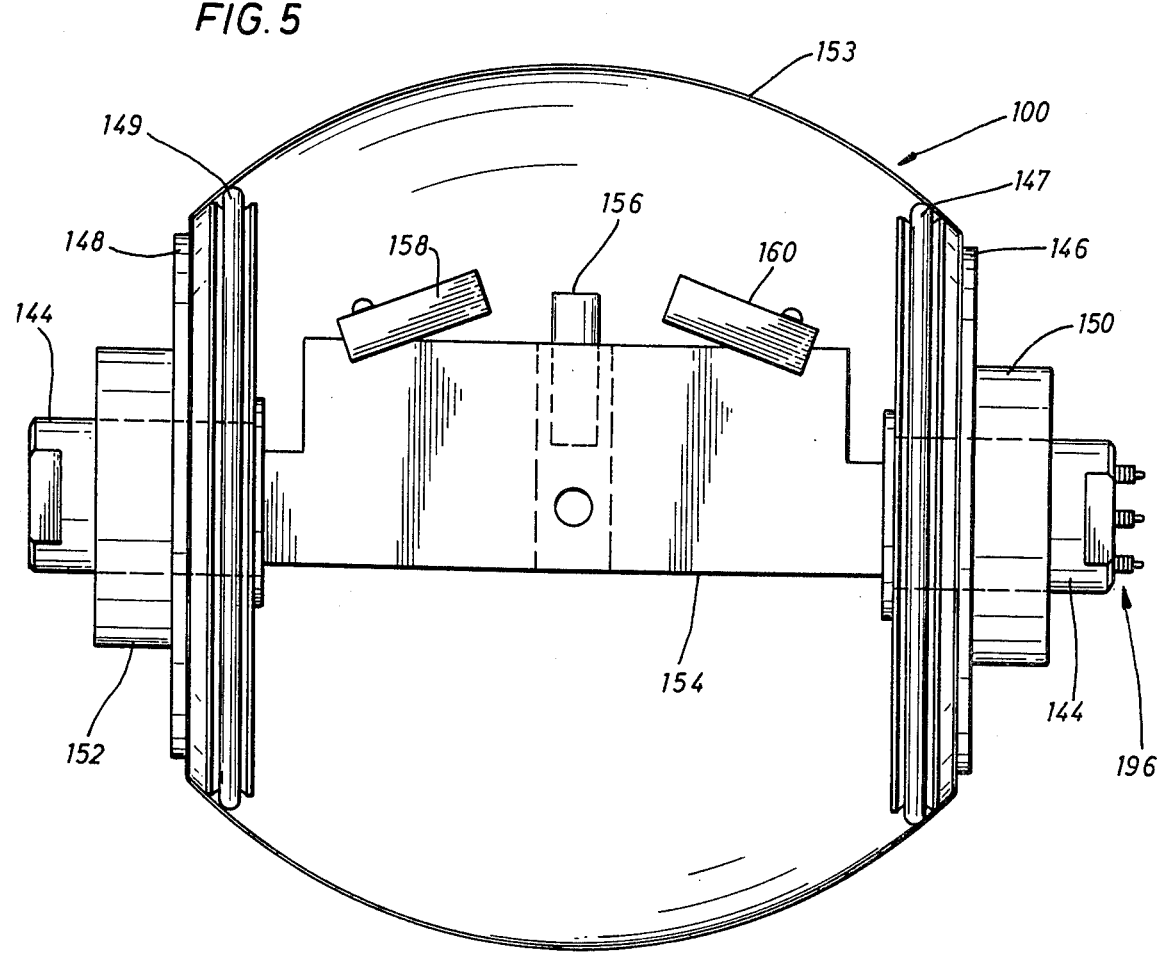
FIG. 5 is a side view of the lengthwise scan wheel assembly with a portion of the bladder broken away to show the transducers.

With reference to FIGS. 5–7, the description will now turn to a detailed description of the inspection wheels which are mounted within the wheel housings of the head assemblies. Preferably, the two inspection wheels present an identical outward appearance and are interchangeable within the two head assemblies. However, the two inspection wheels include ultrasonic transducers mounted at different angles to detect different flaw characteristics in the pipe. The common features of the two inspection wheels are that they include identical bladders and the terminal portions of the respective axles are identical so as to make them interchangeable within the respective head assemblies.

The structure of inspection wheel 100 will first be described with reference to the detailed illustration of FIG. 5. Wheel 100 includes an axle 144 which may be received within appropriate journals in one of the head assemblies. In operation, the axle remains stationary and mounts a pair of circular, rotatable flanges 146, 148 on hubs 150, 152. Flanges 146, 148 include peripheral metal retainer rings which grip the edges of a flexible bladder 153 that houses the transducers. Wear at the interface between the bladder and flanges is minimized by means of O-rings 147, 149 which are mounted in recesses in flanges 146, 148 internal of the bladder. The portion of the inspection wheel inside the bladder comprises a non-rotating yoke 154. Yoke 154 fixedly mounts three ultrasonic transducers 156, 158, 160. Transducer 156 is a cylindrically focused electro-acoustical transducer which is centrally mounted for monitoring wall thickness by transmitting ultrasonic pulses directly into the pipe normal to the pipe surface. Since transducer 156 is substantially cylindrical, it is fixed within a bore made in yoke 154. It has been found that a one-half inch diameter, eight megahertz cylindrically focused transducer of the type manufactured by Harisonics, Inc. of Stamford, Connecticut provides excellent results.

Transducers 158, 160 are fixed within machined slots in yoke 154 so as to transmit pulses outwardly in different directions lengthwise along the pipe. As explained below in connection with FIG. 8, transducers 158, 160 are used to detect transverse defects in the pipe. In a preferred embodiment, transducers 158, 160 are ground focal length transducers.

Wheel 102 will now be described with reference to FIGS. 6 and 7. Wheel 102 includes an axle 166, hubs 168, 170, flanges 172, 174, a bladder 176 and O-rings 178, 180 identical to those illustrated in FIG. 5 in connection with inspection wheel 100. The yoke of wheel 100 and the positioning of the associated transducers differs markedly from those found in wheel 100 since different characteristics of the pipe are being inspected. As shown in FIG. 6, yoke 182 is formed in two pieces comprising an upper yoke member 184 and a lower yoke member 186. Lower member 186 includes a machined recess for slidingly receiving track formed in upper member 184. A pair of ultrasonic transducers 188, 190 are fixed in appropriate machined recesses in upper yoke member 184 so that they may transmit ultrasonic pulses circumferentially on the pipe being inspected to detect longitudinal defects. As shown in FIG. 7, transducer 190 is fixed at an angle so that the beam transmitted will strike the pipe at an angle acute to the longitudinal axis of the pipe and travel around the pipe in one direction, e.g., clockwise. Although not shown in FIG. 7, transducer 188 is fixed to emit a beam traveling in the opposite direction about the pipe, e.g., counterclockwise. As the beams travel from the transducers, they tend to spread. The relative sliding motion between upper and lower yoke members 184, 186 allows an adjustment of the beam paths to correct for any irregularities in the transducers or errors in the fixturing operation. Once the desired relationship between the upper and lower members is achieved, the members may be permanently secured in that position by means of bolts, spot welding, or other suitable means.

The lower yoke member 186 houses a third transducer 192. Transducer 192 is a cylindrically focused transducer identical to transducer 156 illustrated in FIG. 5. Transducer 192 monitors wall thickness and, like transducer 156, is set to focus at approximately the outside surface of the pipe being inspected.

The axles of both inspection wheels include microdot coaxial cable connectors 196 which mate with appropriate recesses in the head assembly journals for hermetically sealing the electrical connection to the transducers.

Figure 8:
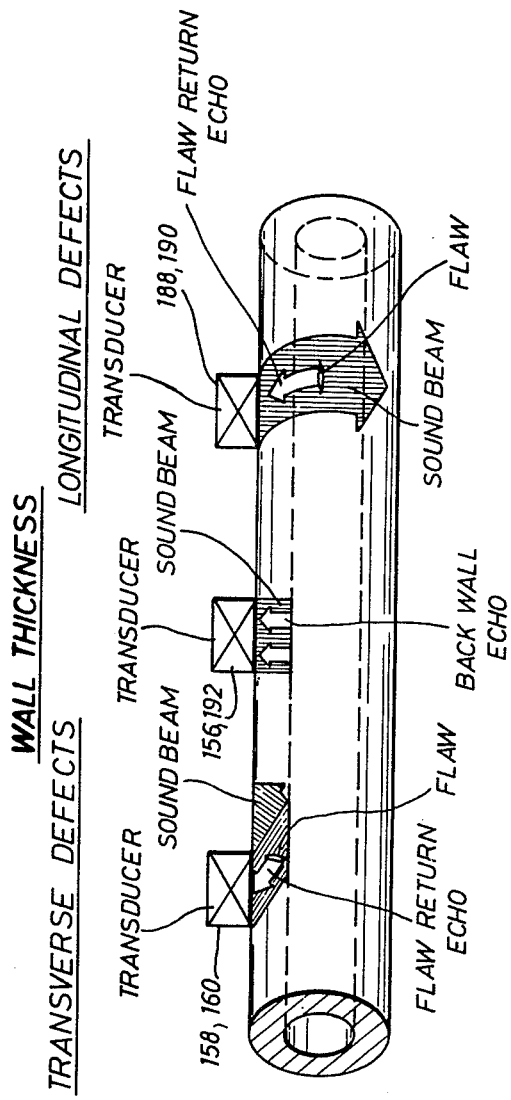
FIG. 8 schematically illustrates the technique used for detection of transverse and longitudinal defects and monitoring of wall thickness.

The ultrasonic testing theory utilized in inspecting pipe in accordance with the present invention will now be discussed with primary reference to FIG. 8. As stated above, cylindrically focused transducers 156, 192 send pulses directly into the pipe to monitor the pipe wall thickness. By means known to those skilled in the art, the back wall echoes are picked up by a signal receiver and a readout indicative of wall thickness is formulated. In a preferred operation, the helical paths transcribed by the two inspection wheels will be tight enough (i.e., with a small enough pitch angle) so that the paths scanned by the transducers 156, 192 will overlap to give a confirming profile of wall thickness for all points on the pipe. Accordingly, the pipe rotation speed and carriage speed are chosen to create an overlap, for example, an overlap wherein the path scanned by the second wall thickness transducer overlaps approximately twenty percent (20%) of the path scanned by the first wall thickness transducer. In a particular embodiment, each transducer 156, 192 transmits a beam that is ¾ inch in a direction parallel to the axis of the pipe. Since the transducers 156, 192 could be spaced in their respective wheels so that their helical areas of coverage just abut, a total spread of 1½ inches could be attained, i.e., a longitudinal movement of 1½ inches for each rotation of the pipe. However, it has been found that a small overlap of the beam spread, e.g., a ¼ inch overlap, gives improved results in monitoring wall thickness. Therefore, it can be seen that according to a preferred manner of practicing the invention, for all sizes of pipe being inspected, the longitudinal movement of the pipe is 1¼ inches per revolution. This means that the pitch angle transcribed in inspecting small diameter pipe is significantly greater than that transcribed when inspecting large diameter pipe.

Longitudinal defects are detected by transducers 188, 190 which are housed within the bladder of inspection wheel 102 (see FIGS. 6 and 7). As shown in FIG. 8, the ultrasonic beam transmitted by each transducers 188, 190 travels circumferentially so that a flaw return echo will be created by a substantially longitudinal flaw in the pipe wall. By having transducers 188, 190 emitting beams in opposite directions, i.e., one clockwise and one counterclockwise, better flaw detection is obtained because certain longitudinal flaws may be very difficult to detect unless the ultrasonic beam approaches it from the right direction.

Transducers 158, 160 which are housed in inspection wheel 100 are utilized to detect transverse defects in the pipe wall. Referring to FIG. 8, it can be seen that the ultrasonic beam travels through the pipe wall and may bounce between the inner and outer surfaces of the wall of the pipe several times before dissipating. If the beam encounters a transverse defect before dissipating, a flaw return echo will return and be detected by the signal receiver associated with the transducer.

Although not forming a part of this invention, it should be pointed out that the ultrasonic inspection equipment includes a master pulse generator to energize the six transducers. The equipment also includes a display in the form of a strip chart recorder or the like to produce a readable response to reflected waves. An audible indication of the existence of flaws may alternatively be provided.

A typical pipe inspection operation will now be described with continued reference to the previous drawings and with particular reference to the control panel illustrated in FIG. 9. For an inspection operation to be carried out at a well site or any location where oil field tubulars, e.g., drill pipe, casing, tubing or line pipe, may be located, portable inspection apparatus 10 is towed to such site with truss section 17 resting on deck 12. At the inspection site the truss section is extended by means of cylinder 18 and the entire inspection apparatus is stabilized by means of legs 14. With the carriage 70 positioned near the control house 16, the first pipe is loaded onto the drive rollers 22 by means of load ramps 34, 36, swing arms 49 and lift cylinders 58. With the first pipe in place, the operator begins to program the processor used for controlling the automated pipe inspection operation. The initial programming includes first setting the carriage at a zero position proximate control house 16. The carriage is then driven toward the end of the pipe until a pair of confronting electric eyes (not shown) at the forward end of the carriage detect the starting end of the pipe. The carriage delays movement for a short period while brush 92 is lowered into contact with the pipe and is driven by its motor to commence cleaning the pipe. The carriage is then driven over the pipe until the first head assembly 126 is positioned over the end of the pipe at which point the distance traversed is stored in the processor and the first head assembly 126 is lowered into contact with the rotating pipe. Similarly, the carriage moves until the second head assembly is over the end of the pipe and that distance is stored in the processor's memory. The carriage is then allowed to traverse the entire length of the pipe until a pair of confronting electric eyes (not shown) at the forward end of the carriage detect the end of the pipe at which time the brush 92 is raised. The head assemblies are sequentially raised as they reach the end of the pipe.

Since the carriage may be driven in both directions, the apparatus is programmed for automated control for inspecting pipe with the carriage moving from the remote end of the apparatus 10 back toward the control house 16. Programming of the carriage movement, brush movement and head assembly movements for the reverse carriage direction is carried out in a fashion identical to that for the forward direction. Once the processor has been programmed as set forth above, a continuous automated pipe inspection operation may commence.

Initially, pipe is loaded from the storage rack 40 by manually placing the pipe on endoe 44. The pipe is brought to the desired starting position by moving it over rollers 44a. According to an automated control operation, dogs 44, which have been situated in their lowered position at endoes 44, pick up a pipe and move it to rest on load decks 41 in response to a command signal from the processor as initiated by the auto start of the Pipe Load. Dogs 44 are then automatically returned to their lower position for the next load sequence.

With a pipe loaded on decks 41, the automated Pipe Transfer On sequence begins by depression of the appropriate auto start switch. First, swing arms 49 move out to their extended positions at which positions a switch (not shown) is actuated causing the processor to trigger the kick cylinders 54, thereby indexing one pipe section onto the swing arms. As the pipe rolls on the swing arms 49 to rest against stops 65, a switch (not shown) triggers the processor to retract the kick cylinders and extend lift cylinders 58. When the lift cylinders reach their extended positions, and remove the pipe from the swing arms, a switch (not shown) triggers the processor to retract the swing arms and the lifted arms are then retracted to place the pipe on rollers 22.

With the pipe on rollers 22 and the carriage operation having been previously programmed in the manner set forth above, the Inspection auto start causes the carriage to traverse the entire length of the pipe while controlling the vertical movement of the brushes and head assemblies.

When the inspection of each pipe is complete, auto start of the Pipe Transfer Off sequence moves the pipe to the top of the ramps of the unload ramps according to a sequence essentially the reverse of the transfer on operation. The Pipe Unload operation moves the inspected pipe down the unload ramp to rack 42.

Figure 9:
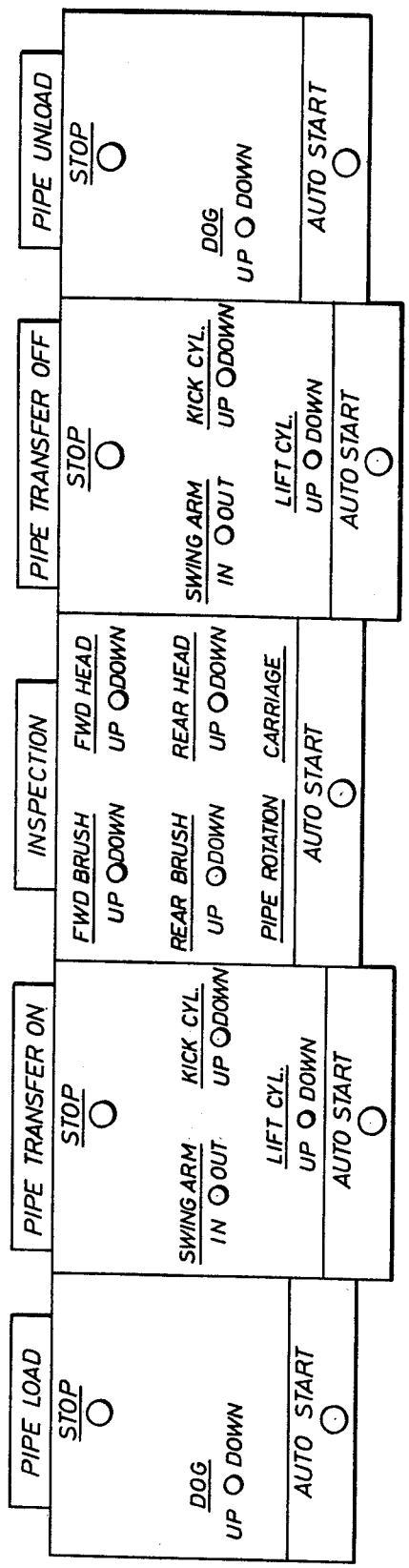
FIG. 9 is a view of the control panel showing means for both automated and manual control.

It will be appreciated from the various controls on the control panel illustrated in FIG. 9 that any or all of the above-described operations may be carried out without automated programmed control.

Alternative Embodiment

Figure 10:
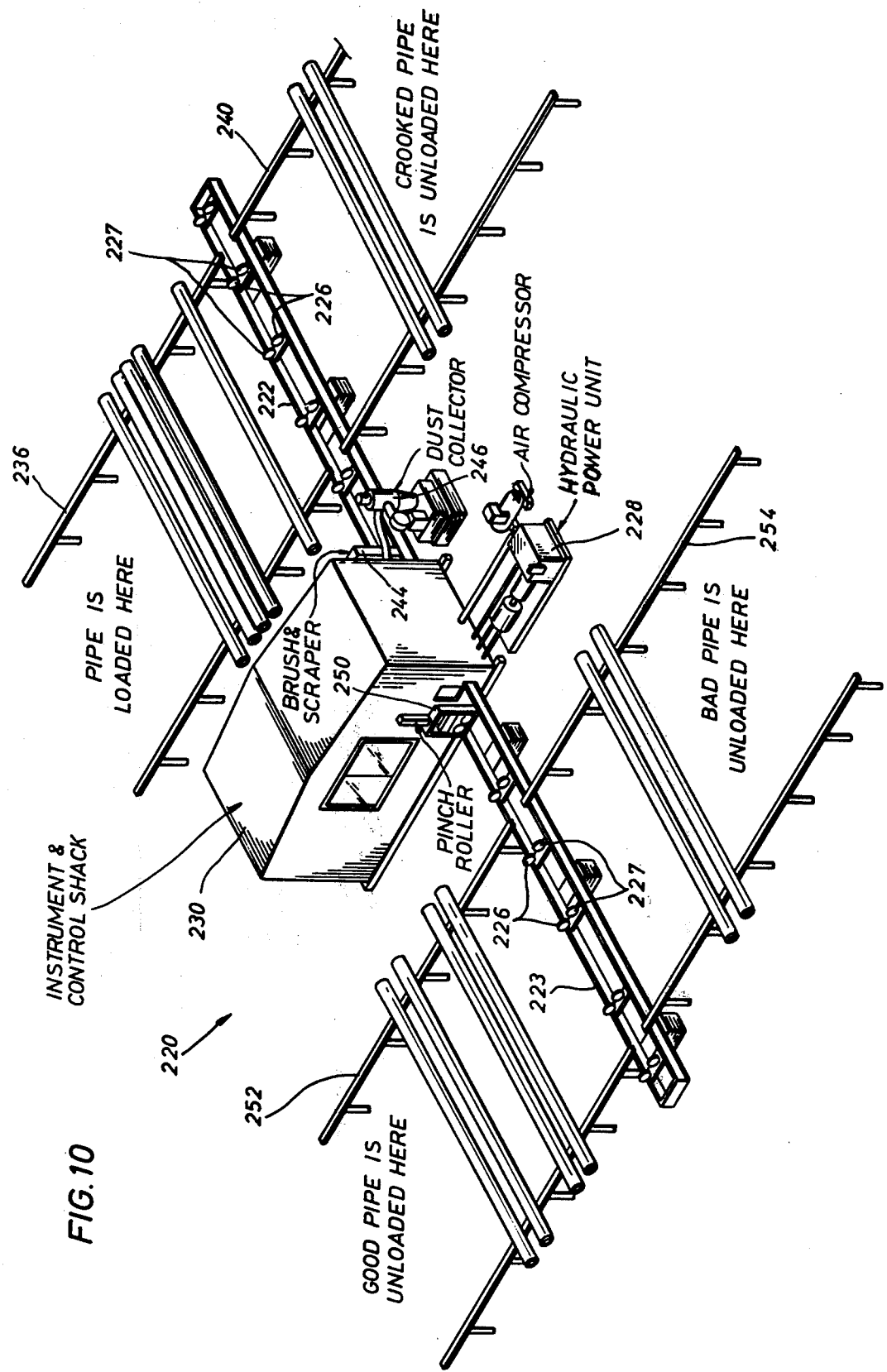
FIG. 10 is a pictorial view of an alternative embodiment of the invention wherein the cylindrical member is driven longitudinally past relatively stationary ultrasonic equipment.

Referring to FIG. 10 the description will now turn to a detailed description of an alternative inspection apparatus 220 wherein the ultrasonic equipment remains stationary while the pipe being inspected is rotating and longitudinally driven past the ultrasonic equipment. The device illustrated in FIG. 10 is intended as a permanent yard unit as opposed to a portable unit which may be easily moved to drilling locations.

Apparatus 220 includes fixed decks 222, 223 which support a series of pairs of drive rollers. Each pair of rollers includes a driven roller 226 powered by an individual hydraulic motor and an idler roller 227. Unlike the previously described rollers 22 illustrated in FIG. 1, rollers 226 not only rotate the pipe about its axis but also drive the pipe longitudinally. The driven roller 226 in each pair is angled forwardly in the direction of pipe travel and rotated somewhat askew so as to impart rotation and axial drive to the pipe. The associated idler roller 227 is angled opposite from the driven roller 226 to support and stabilize the moving pipe.

In the operation of inspection apparatus 220, pipe is loaded on a rack 236 and transferred to rollers 226 by mechanical means which may be programmed for automated remote control. Pipe which is too crooked to pass through the inspection apparatus (as determined by a visual test when rotation starts) is immediately transferred to a deck 240. Straight pipe is driven through house 230 which houses an inspection carriage (not shown) which is identical to the previously described carriage 70 except that it is not mounted on wheels for longitudinal movement. The rotation and longitudinal movement of the pipe enables the inspection wheels to transcribe helical paths on the surface of the pipe so that the inspection operation taking place at the interface of the inspection wheels and the pipe is identical to that described earlier.

As shown in FIG. 10, a brush and scraper 244 is located at the entrance to house 230 to clean the pipe prior to its inspection. A dust collector 246 is provided to collect debris from the cleaning area. At the exit from house 230 there is a pinch roller assembly 250 that facilitates the positioning of the pipe on deck 223 as it leaves the control house. After the pipe has completely left the control house, it is stored on either rack 252 (good pipe) or rack 254 (bad pipe).

The instant invention has been disclosed in connection with specific embodiments. However, it will be apparent to those skilled in the art that variations from the illustrated embodiment may be undertaken without departing from the spirit or scope of the invention. For example, the transducers may be housed in different combinations within the inspection wheels. A different number of inspection wheels could be used, for example, three wheels with a first wheel including transducers for detecting longitudinal defects, a second wheel including transducers for detecting transverse defects and a third wheel including transducers for monitoring wall thickness. It will also be appreciated by those skilled in the art that the apparatus and method of the present invention is applicable to many kinds of cylindrical tubular goods and, in its broadest sense, is not limited to oil field tubular goods. These and other variations will be obvious to those skilled in the art and are within the spirit and scope of the instant invention.

What is claimed:

1. A method of nondestructive ultrasonic testing of tubular members comprising the steps of:
    rotating the member to be inspected about its longitudinal axis;
    providing relative longitudinal movement between a pair of ultrasonic inspection devices and said member; each inspection device including at least two ultrasonic transducers;
    sonically coupling said devices to said member during the rotating and moving steps;
    scanning said member circumferentially by a first pair of transducers mounted within a first inspection device, said first pair transmitting sonic beams in opposite directions around the member to detect longitudinal flaws;
    scanning said member lengthwise by a second pair of transducers mounted within a second inspection device, said second pair transmitting beams in opposite directions along the length of the member to detect transverse flaws; and
    analyzing the reflected beams for display.

2. A method as claimed in claim 1 wherein said inspection devices are wheels having a relatively flexible bladder for contacting the member and including the step of urging said wheels into contact with the surface of said member during said rotating and moving steps at a substantially constant pressure.

3. A method as claimed in claim 1 including the step of monitoring wall thickness by a fifth transducer mounted within the first inspection device and as sixth transducer mounted within the second inspection device, said fifth and sixth transducers transmitting sonic beams directly into the member substantially normal to the axis of the member.

4. A method as claimed in claim 3 wherein said fifth and sixth transducers are spaced from each other within their respective wheels in such a manner that the leading one of said fifth and sixth transducers traces a first helical path having a predetermined width and the trailing transducer traces a second helical path that at least partially overlaps the first helical path.

5. An ultrasonic inspection wheel useful for tracing a substantially helical path on a cylindrical member having a bore, comprising:
    axle means having terminal end portions adapted for fixed mounting in appropriate journals;
    a fixed central yoke forming a continuation of said axle means and being disposed between said axle terminal end portions substantially along the axis of the wheel;
    a pair of on-line transducers mounted by said yoke for transmitting sonic beams in opposite directions along the length of the pipe for detecting transverse flaws;
    electrical connector means for supplying pulsed energy to said transducers;
    flanges rotatably mounted proximate the ends of said yoke; and
    a flexible bladder having two open ends, each end being mounted on a respective one of said flanges.

6. An ultrasonic inspection wheel as claimed in claim 5 wherein each of said pair of transducers is located by and mounted in machined slots in said yoke.

7. An ultrasonic inspection wheel as claimed in claim 5 wherein said yoke mounts a cylindrically focused transducer for transmitting sonic beams directly into the member.

8. An ultrasonic inspection wheel as claimed in claim 7 wherein said cylindrically focused transducer is mounted in a bore in the yoke.

9. An inspection wheel as claimed in claim 5 including an O-ring mounted on each of said flanges internal of the bladder for protecting against wear between the bladder and the flange.

10. An ultrasonic inspection wheel useful for tracing a substantially helical path on a cylindrical member having a bore, comprising:
    axle means having terminal end portions adapted for fixed mounting in appropriate journals;
    a fixed central yoke forming a continuation of said axle means and being disposed between said axle terminal end portions substantially along the axis of the wheel;
    a pair of on-line transducers mounted by said yoke for transmitting sonic beams in opposite directions circumferentially around the member for detecting longitudinal flaws;
    electrical connector means for supplying pulsed energy to said transducers;
    flanges rotatably mounted proximate the ends of said yoke; and
    a flexible bladder having two open ends, each end being mounted on a respective one of said flanges.

11. An ultrasonic inspection wheel as claimed in claim 10 wherein said yoke is formed in two pieces, a first piece being fixed with respect to the wheel axis and a second piece being movable with respect to said first piece, said pair of transducers being mounted on said second piece to allow adjustment of the beam paths transmitted by said pair of transducers.

12. An ultrasonic inspection wheel as claimed in claim 10 wherein said yoke mounts a cylindrically fo-